(12) United States Patent
Kensil

(10) Patent No.: US 6,231,859 B1
(45) Date of Patent: May 15, 2001

(54) SAPONIN ADJUVANT COMPOSITIONS

(75) Inventor: Charlotte A. Kensil, Milford, MA (US)

(73) Assignee: Aquila Biopharmaceuticals, Inc., Framingham, MA (US)

( * ) Notice: Subject to any disclaimer, the term of this patent is extended or adjusted under 35 U.S.C. 154(b) by 0 days.

(21) Appl. No.: 08/982,731

(22) Filed: Dec. 2, 1997

Related U.S. Application Data

(60) Provisional application No. 60/032,080, filed on Dec. 2, 1996.

(51) Int. Cl.[7] ............................. A61K 39/00; A61K 39/39
(52) U.S. Cl. ................................. 424/184.1; 424/278.1; 424/283.1; 514/25
(58) Field of Search ................. 514/25; 424/184.1, 424/278.1, 283.1

(56) References Cited

U.S. PATENT DOCUMENTS 5,057,540 * 10/1991 Kensil et al. ........................... 514/25
5,583,112 * 12/1996 Kensil et al. ........................... 514/25

FOREIGN PATENT DOCUMENTS

WO 96/11711   4/1996  (WO) .

OTHER PUBLICATIONS

Kensil, C.R., et al. J. Immunol. 146:431–437, Jan. 15, 1991.*
Newman, M.J. et al. J. Immunol. 148:2357–2362, Apr. 15, 1992.*

* cited by examiner

*Primary Examiner*—David Saunders
(74) *Attorney, Agent, or Firm*—Hale and Dorr LLP

(57) ABSTRACT

The present invention is in the field of medicinal chemistry. In particular, the invention is related to vaccines comprising novel combinations of saponin adjuvants, to pharmaceutical compositions and vaccines comprising these novel combinations, to methods of using these novel combinations to enhance the immune response of an individual to an antigen, and to the use of the novel combinations to increase the immunogenicity of vaccines.

12 Claims, 11 Drawing Sheets

SAPONIN ADJUVANT COMPOSITIONS

CROSS REFERENCE TO RELATED APPLICATION

This application is related to U.S. Provisional Application No. 60/032,080, filed Dec. 2, 1996, abandoned, the disclosure of which is fully incorporated herein by reference.

BACKGROUND OF THE INVENTION

1. Field of the Invention

The present invention is in the field of medicinal chemistry. In particular, the invention is related to vaccines comprising novel combinations of saponin adjuvants, to pharmaceutical compositions and vaccines comprising these novel combinations, to methods of using these novel combinations to enhance the immune response of an individual to an antigen, and to the use of the novel combinations to increase the immunogenicity of vaccines.

2. Brief Description of the Background Art

Quillaja saponins are a mixture of triterpene glycosides extracted from the bark of the tree *Quillaja saponaria*. They have long been recognized as immune stimulators that can be used as vaccine adjuvants, (Campbell, J. B., and Peerbaye, Y. A., *Res. Immunol.* 143(5):526–530 (1992)), and a number of commercially available complex saponin extracts have been utilized as adjuvants. Crude saponins have been extensively employed as adjuvants in vaccines against foot and mouth disease, and in amplifying the protective immunity conferred by experimental vaccines against protozoal parasites such as *Trypanosoma cruzi* plasmodium and also the humoral response to sheep red blood cells (SRBC). (Bomford, *Int. Arch. Allerg. Appl. Immun.* 67:127 (1982)).

The first commercially available Quillaja saponin adjuvants were crude extracts which, because of their variability, were not desirable for use in veterinary practice or in pharmaceutical compositions for man. An early attempt to purify Quillaja saponin adjuvants was made by Dalsgaard, *Archiv fuer die gesamte Virusforschung* 44:243 (1974). Dalsgaard partially purified an aqueous extract of the saponin adjuvant material from *Quillaja saponaria Molina*. However, while Dalsgaard's preparation, "Quil-A," was a definite improvement over the previously available commercial saponins, it still exhibited considerable heterogeneity.

Subsequent analysis via high-pressure liquid chromatography showed that Quil A was in fact a heterogeneous mixture of structurally related compounds. (U.S. Pat. No. 5,057,540; Kersten, G. F. A. et al., *Infect. Immun.* 56:432–438 (1988); Kensil, C. R. et al., *J. Immunol.* 146:431–437 (1991); Kensil, C. R. et al., *J. Am. Vet. Med. Assoc.* 199:1423–1427 (1991)). However, not all of these saponins were active as adjuvants.

The four most predominant purified Quillaja saponins are QS-7, QS-17, QS-18, and QS-21 (alternatively identified as QA-7, QA-17, QA-18, and QA-21). These saponins have been purified by HPLC and low pressure silica chromatography and were found to be adjuvant active, although differing in biological activities such as hemolysis and toxicity in mice. In particular, QS-21 and QS-7 were found to be least toxic in mice. (Kensil, C. R. et al., *J. Immunol.* 146:431–437 (1991)).

Due to its potent adjuvant activity and low toxicity, QS-21 (commercially available as the "Stimulon®" adjuvant) has been identified as a useful immunological adjuvant. (Kensil, C. R. et al., "Structural and Immunological Characterization of the Vaccine Adjuvant QS-21," in *Vaccine Design: The Subunit and Adjuvant Approach*, Powell, M. F. and Newman, M. J. eds., Plenum Press, New York (1995)). QS-21 is a complex triterpene glycoside of quillaic acid. QS-21 is glycosylated at triterpene carbon 3, triterpene carbon 28, and carbon 5 of the second fatty acyl unit in a fatty acid domain.

More recently, QS-21 was further purified using hydrophilic interaction chromatography (HILIC) and resolved into two peaks, QS-21-V1 and QS-21-V2, which have been shown to be chemically different compounds. In C57BL/6 mice immunized with vaccines consisting of ovalbumin and either QS-21, QS-1-V1, or QS-21-V2, both of the individual components QS-21-V1 and QS-21-V2 are comparable in adjuvant effect to the original QS-21 peak (containing a mixture of 3:2 QS-21-V1 and QS-21-V2) for boosting the IgG subclasses IgG1, IgG2b, and IgG2 as well as the total IgG titer. (Co-pending U.S. patent application No. 07/906,880, U.S. Pat. No. 5,583,112, the entire contents of which is hereby incorporated by reference).

Quillaja saponins are structurally distinct from the saponins derived from other plant species. Two structural features that distinguish *Quillaja saponaria* saponins from those of other plant species are a fatty acid domain and a triterpene aldehyde at carbon 4 of the triterpene. (Kensil, C. R. et al., "Structural and Immunological Characterization of the Vaccine Adjuvant QS-21," in *Vaccine Design: The Subunit and Adjuvant Approach*, Powell, M. F. and Newman, M. J. eds., Plenum Press, New York (1995)). Modifications to the aldehyde on the triterpene indicate that this functional group may be involved in the adjuvant mechanism (Soltysik, S. et al., *Vaccine* 13(15):1403–1410 (1995)).

Quillaja saponins, particularly QS-7, QS-17, QS-18, and QS-21, have been found to be excellent stimulators of antibody response to soluble T-dependent protein antigens, "subunit antigens", which are poorly immunogenic and require a potent adjuvant for maximization of immune responses. Examples of purified subunit antigens for which saponin adjuvants will augment the IgG response in mice include keyhole limpet hemocyanin (KLH), HIV-1 gp120 (Bomford, R. et al, *AIDS Res. Hum. Retroviruses* 8:1765 (1992)), and influenza nucleoprotein (Brett, S. et al., *Immunology* 80:306 (1993)). QS-7, QS-17, QS-18 and QS-21 have also been shown to stimulate potent antibody responses in mice to the antigens bovine serum albumin and cytochrome $b_5$ (Kensil, C. R. et al., *J. Immunol.* 146:431 (1991)). The level of antibody response induced by these purified saponins was comparable to other commonly used adjuvants, e.g., complete Freund's adjuvant, and superior to aluminum hydroxide.

QS-21 has also been shown to enhance antibody responses to T-independent antigens, including unconjugated bacterial polysaccharides (White, A. C. et al., "A purified saponin acts as an adjuvant for a T-independent antigen, in: *Immunobiology of Proteins and Peptides*, Vol. VI (M. Z. Atassi, ed.), Plenum Press, New York, pp. 207–210 (1991)). The immunogenicity of the vaccine was further increased by conjugating diphtheria toxoid to the polysaccharide. QS21 enhanced the antibody response to the polysaccharide as well as the carrier, including IgG2a, IgG2b, and IgG3 responses. (Coughlin, R. T. et al., *Vaccine* 13(1):17–21 (1995)).

The ability of adjuvants to modulate the isotype distribution and IgG subclass distribution of antibody response to an antigen through the promotion of Ig subclass switching has important implications for immunity to many bacterial and viral vaccines. QS-7, QS-17, QS-18, and QS-21 stimulate IgG2a response to cytochrome b5 after administration with saponin doses of 20 µg (Kensil, C. R. et al., *J. Immunol* 146:431 (1991)). In this regard, QS-21 shifts predominant IgG1 responses to a profile that includes significant IgG2b and IgG2a responses. For example, QS-21 has been shown to stimulate antigen-specific IgG2a to a number of antigens, including *Borrelia burgdornferi* outer surface proteins OspA and OspB (Ma, J. et al., *Vaccine* 12(10):925 (1994)), feline leukemia virus (FeLV), envelope gp70 (Kensil, C. R. et al., *J. Am. Vet. Med. Assoc.* 10:1423 (1991)), human cytomegalovirus (HCMV) envelope protein gB (Britt, W. et al., *J. Infect. Dis.* 171:18 (1995)), respiratory synctial virus (RSV) purified fusion protein (Hancock, G. E. et al., *Vaccine* 13(4):391 (1995)), and tetanus toxoid (Coughlin, R. T. et al., *Vaccine* 13(1):17 (1995)). QS-21 has also been shown to induce boostable antibody responses. (Britt et al., *J. Infect. Dis.* 171:18–25 (1995); Helling et al., *Cancer Res.* 55:2783–2788 (1995)).

The ability of the QS-21 adjuvant to induce class I major histocompatibility complex (MHC) antigen-restricted cytotoxic T-lymphocyte responses (CTL) after immunization with soluble proteins is a characteristic of saponin adjuvants. A number of studies have shown the ability of QS-21 to induce potent cytotoxic T-lymphocyte (CTL) responses to various antigens, including ovalbumin (Wu, J.-Y. et al., *Cell. Immunol.* 154:394–406 (1994); Newman, M. J. et al., *J. Immunol.* 148(8):2357–2362 (1992)), recombinant HIV-1 gp160 protein (Wu, J.-Y. et al., *J. Immunol.* 148:1519 (1992)), and subunit $SIV_{mac251}$ gag and env (Newman, M. J. et al., *AIDS Res. Hum. Retroviruses* 10(7):853 (1994)).

Most of the saponin adjuvant studies have been carried out in mice. However, the adjuvant activity of saponins is not limited to mice; it has also been demonstrated in guinea pigs, rabbits, pigs, sheep, cattle, and nonhuman primates. An adjuvant effect from QS-21 has been observed in cats, guinea pigs, dogs, nonhuman primates, and humans. (Kensil, C. R. et al., "Structural and Immunological Characterization of the Vaccine Adjuvant QS-21," in *Vaccine Design: The Subunit and Adjuvant Approach*, Powell, M. F. and Newman, M. J. eds., Plenuim Press, New York (1995)).

Phase 1 human trials of QS-21 with GM2 ganglioside-keyhole limpet haemocyanin conjugate vaccine have been conducted in patients with malignant melanoma (Livingston, P. O. et al., *Vaccine* 12:1275–1280 (1994). Increased immunogenicity after administration with QS-21 adjuvant was observed (Helling, F. et al., *Cancer Res.* 55:2783–2788 (1995)). In another set of clinical trials, QS-21 was found to be a potent immunological adjuvant that significantly increased the serological response of melanoma patients to the murine antiidiotype antibody MELIMMUNE-1 (Livingston, P. O. et al., *Vaccine Res.* 4(2):87 (1995).

A number of studies discuss the use of Quillaja saponins, particularly QS-21, in conjunction with other adjuvants. For example, QS-21 was shown to be an effective co-adjuvant with aluminum hydroxide (alum)—absorbed antigens. (Ma, J.-Y. et al., *Vaccine* 12(10):925–933 (1994); Newman, J. et al., *J. Immunol.* 148(8):2357–2362 (1992); Kensil, C. R. et al., "Structural and Immunological Characterization of the Vaccine Adjuvant QS-21," in *Vaccine Design: The Subunit and Adjuvant Approach*, Powell, M. F. and Newman, M. J. eds., Plenum Press, New York (1995); Kensil et al., *J. Am. Vet. Med. Assoc.* 199:1423–1427 (1991); Wu, J.-Y. et al., *J. Immunol.* 148:1519–1525 (1992); Kensil et al., *Vaccine Res.* 2:273–281 (1993)). Moreover, the use of mixtures of two or more saponin adjuvants is discussed in U.S. Pat. No. 5,057,540, and currently co-pending U.S. patent application No. 07/906,880 (now U.S. Pat. No. 5,583,112) (The entire contents of both of these documents are hereby incorporated by reference.)

The immune adjuvant effect of saponins is dependent upon dose. Depending upon the antigen and the species, a minimum dose level of QS-21 is required for optimum response. (Kensil, C. R. et al., *J. Immunol.* (1991); Kensil, C. R. et al., *Vaccine Res.* (1993); Newman et al., *J. Immunol.* (1992); Livingston, et al., *Vaccine* (1994). Below this minimum dose, the immune adjuvant effect is suboptimal (either low level or absent). QS-7 also has a dose response curve. (Kensil, C. R. et al., *J. Immunol.* (1991)).

Until now, however, the identification of combinations of two or more Quillaja saponins in suboptimal doses to produce a synergistic adjuvant effect was unknown in the art.

SUMMARY OF THE INVENTION

Figure 1:
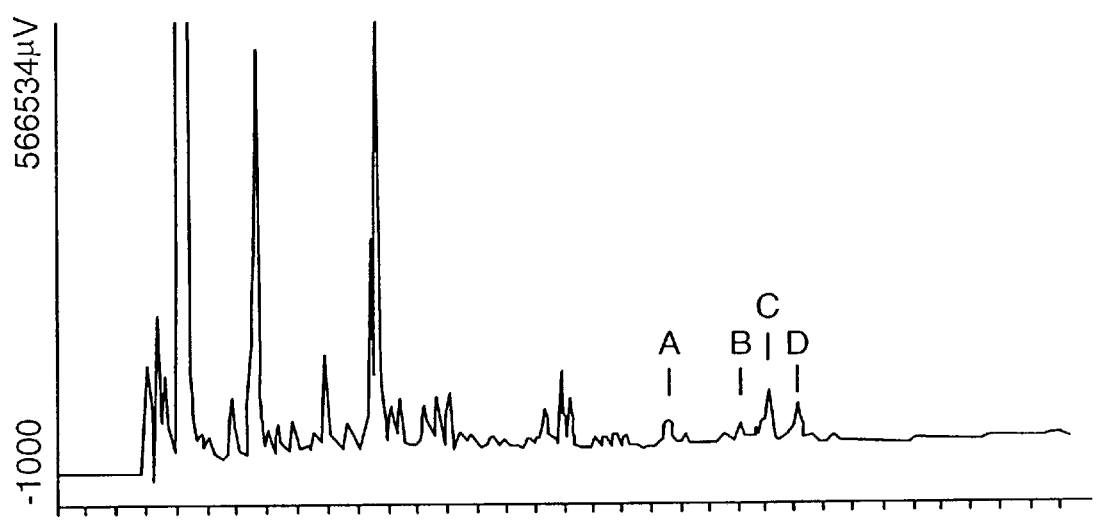
FIG. 1 shows a reversed phase HPLC analysis of a typical *Quillaja saponaria* bark extract that is suitable for the purification of the saponins used in the present invention. The major saponin adjuvants QS-7, QS-17, QS-18, and QS-21 are marked on the chromatogram, as "a", "b", "c", and "d", respectively.

Applicants have now discovered, unexpectedly, that the combination of suboptimal doses of the substantially purified QS-7 and QS-21 saponins produce a synergistic adjuvant effect rather than the expected additive effect.

Accordingly, the present invention is directed to a saponin composition having immune adjuvant activity comprising two or more substantially pure saponins.

The present invention is also directed to a saponin composition having immune adjuvant activity comprising two or more substantially pure saponins from *Quillaja saponaria* in doses that are otherwise suboptimal for the individual saponins.

In a preferred embodiment, the novel saponin composition consists essentially of substantially pure saponins QS-7 and QS-21.

The present invention is also directed to a saponin composition having immune adjuvant activity consisting essentially of substantially pure saponins QS-7 and QS-21-V1.

The present invention is also directed to a saporni composition having immune adjuvant activity consisting essentially of substantially pure saponins QS-7 and QS-21-V2.

The present invention is further directed to a pharmaceutical composition useful for inducing an immune response to an antigen in an individual comprising these saponin compositions and an immunogenically effective amount of an antigen. In one embodiment, the antigen is conjugated to at least one of the substantially pure saponins either directly or through a linker group.

The present invention is further directed to a vaccine comprising such pharmaceutical compositions and a pharmaceutically acceptable carrier.

The present invention is further directed to a method for enhancing an immune response to an antigen in an individual comprising coadministering two or more substantially pure saponins from *Quillaja saponaria* in doses that are otherwise suboptimal for the individual saponins.

The present invention is further directed to a method for enhancing an immune response to an antigen in an individual comprising coadministering an effective amount of substantially pure saponins QS-7 and QS-21.

The present invention is further directed to a method for enhancing an immune response to an antigen in an individual comprising coadministering an effective amount of substantially pure saponins QS-7 and QS-21-V1.

The present invention is further directed to a method for enhancing an immune response to an antigen in an individual comprising coadministering an effective amount of substantially pure saponins QS-7 and QS-21-V2.

In a preferred embodiment, an immunogenically effective amount of an antigen is coadministered with QS-7 and either QS-21, QS-21-V1, or QS-21-V2, or QS-7 and a mixture of QS-21, QS-21-V1, and/or QS-21-V2.

DESCRIPTION OF THE PREFERRED EMBODIMENTS

The saponins of the present invention may be obtained from the tree *Quillaja saponaria Molina*.

The term "saponin" as used herein includes glycosidic triterpenoid compounds which produce foam in aqueous solution, have hemolytic activity in most cases, and possess immune adjuvant activity. The invention encompasses the saponin per se, as well as natural and pharmaceutically acceptable salts and pharmaceutically acceptable derivatives. The term "saponin" also encompasses biologically active fragments thereof.

It has now been discovered that when doses of the QS-7 and QS-21 (and/or QS-21-V1 and/or QS-21-V2) saponins that are suboptimal in achieving an antigen effect when administered independently of one another are coadministered with antigen, the combination produces a synergistic adjuvant effect that is considerably higher than the additive effect expected of such a combination.

The invention concerns compositions comprising a combination of two or more substantially purified saponins from *Quillaja saponaria*, used together in a mixture in doses that would4be suboptimal if these saporins were used separately. The invention concerns compositions, such as immunologic compositions, comprising a combination of substantially pure saponins QS-7 and either QS21, QS-21-V1, or QS-21-V2 or fractions or hydrolytic products thereof which may be linked to an antigen, and methods of using these compositions as vaccines and immune adjuvants. Mixtures of QS-21, QS-21-V1, and QS21-V2 may also be used in combination with QS-7, as opposed to the individual saponins.

The term "immune adjuvant," as used herein, refers to compounds which, when administered to an individual or tested in vitro, increase the immune response to an antigen in the individual or test system to which said antigen is administered. Some antigens are weakly immunogenic when administered alone or are toxic to the individual at concentrations which evoke immune responses in said individual. An immune adjuvant may enhance the immune response of the individual to the antigen by making the antigen more strongly immunogenic. The adjuvant effect may also lower the dose of said antigen necessary to achieve an immune response in said individual.

By the term "coadminister" or "coadministering" is intended that each of at least two components be administered during a time frame wherein the respective periods of biological activity overlap. Thus the term includes sequential as well as coextensive administration of the saponins and saponin compositions of the present invention.

The immunogenic activity of the saponin compositions of the present invention may be determined by any of a number of methods known to those of ordinary skill in the art. The increase in titer of antibody against a particular antigen upon administration of the vaccines and/or adjuvants of the invention may be used as a criteria for immunogenic activity (Dalsgaard, K., *Acta Vetetinia Scandinavica* 69:1–40 (1978); Scott et al., *Int. Archs. Allergy Appl. Immun.* 77:409–412 (1985)). Briefly, one such test involves injecting CD-1 mice intradermally with a saponin composition/antigen conjugate which may be mixed with varying amounts of a potential adjuvant. Sera is harvested from the mice two weeks later and tested by ELISA for anti-immunogen antibody.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

"QS-21" designates the mixture of components QS-21-V1 and QS-21-V2 which appear as a single peak on reverse phase HPLC on Vydac C4 column (5 μm particle size, 300 Å pore, 4.6 mm ID×25 cm1) in 40 mM acetic acid in methanol/water (58/42, v/v). The component fractions are referred to specifically as QS-21-V1 and QS-21-V2 when describing experiments or results performed on the further purified components.

There are multiple acceptable techniques for extraction and isolation of saponins from *Quillaja saponaria Molina* bark. Acceptable procedures for purifying the saponins of the present invention from *Quillaja saponaria Molina* bark, measuring the saponins for immune adjuvant activity, and characterizing the substantially pure saponins are disclosed in U.S. Pat. No. 5,057,540 and U.S. application Ser. No. 07/906,880 (now U.S. Pat. No. 5,583,112), the entire contents of which are hereby incorporated by reference.

Aqueous extracts of *Quillaja saponaria* bark are also available commercially. These are dark brown, foamy extracts that contain many compounds (tannins, polyphenolics, saponins) that can be analyzed by a method such as reversed phase HPLC.

An example of a reversed phase HPLC analysis of a typical bark extract that is suitable for purification of saponins is shown in FIG. 1. The saponin adjuvants QS-7, QS-17, QS-18, and QS-21 are shown, as "a", "b", "c", and "d", respectively. Other minor saponins with adjuvant activity have also been described.

Partial purification to enrich the saponin fraction and to remove the majority of tannins and polyphenolics can be accomplished by dialysis of the extract against water through a 10,000 molecular weight membrane. The saponin fraction is retained.

Alternatively, an aqueous saponin extract can be pretreated with polyvinylpolypyrrolidone to remove high molecular weight tannins and polyphenolics through absorption of these compounds.

Residual tannins and polyphenolics can then be removed from the saponin fraction by diafiltration against water. The saponin fraction, which forms micelles, is retained by ultrafiltration membranes of 10,000 to 30,000 molecular weight cutoff pore size. This yields a partially purified extract that consists predominantly of diverse saponins.

Separation of saponins can be accomplished by chromatography in organic solvents or organic solvent/water mixtures. A separation of saponins on silica was described in U.S. Pat. No. 5,057,540. This yields saponins of intermediate purity (enriched in an individual saponin, but less than substantially pure).

Alternatively, other solvent systems on silica gel or the use of reverse phase chromatography can be used to accomplish the initial separation of saponins. This initial purification step can then typically be followed by reversed phase chromatography or similar HPLC step to purify the saponins to near homogeneity.

The substantially pure saponins useful in the present invention may also be isolated from fresh plant material consisting of substantially living cells as disclosed in WO 95/09179, the entire contents of which is hereby incorporated by reference. For example, saponin extract may be recovered from plant cell material freshly extracted from approximately 15 year-old Quillaja trees. Dialyzed extract is then purified on an ion exchange column, e.g., the DE-52 type, followed by Sephadex G50 gel filtration. Ultrafiltration may be used instead of gel filtration. The purified saponin composition is then subjected to RP-HPLC analysis on a VYDAC C4column, eluted with 30–45% acetonitrile in a 0.15% aqueous TFA-solution.

The same procedure may be performed on plant cell material obtained by means of tissue culture or suspension cell culture.

The saponin compositions of the invention are useful as vaccines which induce active immunity toward antigens in individuals. Preferably, such individuals are humans; however the invention is not intended to be so limiting. Any animal which may experience the beneficial effects of the vaccines of the invention are within the scope of animals which may be treated according to the claimed invention.

The saponin compositions of the present invention exhibit adjuvant effects when administered over a wide range of dosages and a wide range of ratios to the antigen being administered. In one embodiment, the saponin composition is administered in a ratio of adjuvant to immunogen (w/w) of 3.0 or less, preferably 1.0 or less.

The saponin compositions of the invention may be administered either individually or admixed with other substantially pure adjuvants to achieve the enhancement of the immune response to an antigen.

In the present invention, the two substantially pure saponins effective at producing a synergistic effect when coadministered are QS-7 and QS-21. The combination of QS-7 and QS-21 may also be administered together with non-saponin adjuvants. Such non-saponin adjuvants useful with the present invention are oil adjuvants (for example, Freund's Complete and Incomplete), liposomes, cholesterol, mineral salts (for example, $AlK(SO_4)_2$, $AlNa(SO_4)_2$, $AlNH_4(SO_4)$, silica, alum, $Al(OH)_6$, $CA_3(PO_4)_2$, kaolin, and carbon), poly-nucleotides (for example, poly IC and poly AU acids), and certain natural substances or derivatives (for example, wax D from *Mycobacterium tuberculosis*, monophosphoryl lipid A (*Salmonella minnesota*) as well as substances found in *Corynebacterium parvum, Bordetella pertussis*, and members of the genus Brucella), bovine serum albumin, diphtheria toxoid, tetanus toxoid, edestin, keyhole-limpet hemocyanin, Pseudomonal Toxin A, choleragenoid, cholera toxin, pertussis toxin, viral proteins, and eukaryotic proteins such as interferons, interleukins, or tumor necrosis factor. Such proteins or active fragments may be obtained from natural or recombinant sources according to methods known to those skilled in the art. Other known immune-potertiating macromolecules which may be used in the practice of the invention include, but are not limited to, polysaccharides, DNA/RNA nucleotides, tRNA, nonmetabolizable synthetic polymers such as polyvinyl-amine, polymethacrylic acid, polyvinylpyrrolidone, mixed polycondensates (with relatively high molecular weight) of 4'4' diaminodiphenyl-methane-3,3'-dicarboxylic acid and 4-nitro-2-aminobenzoic acid (See Sela, M., *Science* 166:1365–1374 (1969)) or glycolipids, lipids or carbohydrates.

The saponin compositions of the present invention may be directly linked to the antigen or may be linked via a linking group as disclosed in U.S. Pat. No. 5,057,540 and U.S. application Ser. No. 07/906,880 (now U.S. Pat. No. 5,583,112), the entire contents of which are hereby incorporated by reference.

The saponin compositions of the present invention may be utilized to enhance the immune response to any antigen. Typical antigens suitable for the immune-response provoking compositions of the present invention include antigens derived from any of the following, as well as other sources: viruses, such as influenza virus, herpes simplex virus, feline leukemia virus, feline immunodeficiency virus, HIV-1, HIV-2, rabies virus, measles virus, hepatitis B virus, or hoof and mouth disease virus; bacteria, such as *Streptococcus pneumoniae, Staphylococcus aureus, Escherichia coli, Bacillus anthracis, Corynebacterium diphtheriae, Borrelia burgdorferi, Mycobacterium tuberculosis*, or granulocytic and monocytic Ehrlichia; protozoans, such as *Babeosis bovis* or Plasmodium; cancer, e.g., melanoma; parasites, prions (e.g. mad-cow disease), and auto immune disease. The antigens may be proteins, peptides, monosaccharides, polysaccharides, lipopolysaccharides, lipoproteins, and DNA or RNA nucleotides. The proteins, peptides and nucleic acids may be purified from a natural source, synthesized by means of solid phase synthesis, or may be obtained by means of recombinant genetics.

Administration of the saponin compositions useful in the method of present invention may be by parenteral, intravenous, intramuscular, subcutaneous, intranasal, oral, or any other suitable means. The dosage administered may be dependent upon the species, age, weight, kind of concurrent treatment, if any, and nature of the antigen administered. The saponin compositions of the present invention may be administered in any therapeutically effective dosage. A therapeutically effective dosage is any dosage that tends to stimulate an immune response to antigen. Preferably, the novel saponin compositions of the present invention are administered to a human patient in a dosage of from 5 μg–25 μg QS-21, and from 100 μg to 400 μg QS-7. Other therapeutic compositions that may fall outside of this range (e.g., due to the use of different purified saponins, antigen, or species) may be defined by determining suboptimal and optimal doses of each of the two purified saponins, used alone, in a dose-ranging study with a given antigen in a given species. The therapeutic composition would consist of dosages of two or more saponins where each are combined in doses in the suboptimal range when used individually, but where the same doses in a mixture in a composition provide the desired activity.

The maximum possible adjuvant effect for an adjuvant such as QS-21, QS-7, or other purified saponins can be defined by the use of a dose response curve for a given antigen or species. This curve will typically define doses that yield the maximum possible enhancement of immune response. The difference between this maximum immune response and the immune response to a nonadjuvanted formulation can be defined as a value "x". This value "x" can be measured as an antigen-specific antibody titer (non-log transformed) and/or as a % of cytolytic activity due to cytotoxic T lymphocytes at a given effector:target ratio. A suboptimal adjuvant response will typically be 20% or less of "x". The desired adjuvant response will typically be at least 50% or more of "x".

The effective saponin compositions useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the methods of the present invention.

The saponin compositions of the present invention can be combined successfully with vehicle adjuvants. For example, the saponin compositions may be combined in antigen/saponinisterol (preferably cholesterol) immune-stimulating complexes (ISCOMS) and ISCOM matrices as disclosed in Morein, B. et al., *Nature* 308:457 (1984), the entire contents of which are hereby incorporated by reference. An acceptable procedure for preparation of ISCOMS comprises solubilization of amphipathic antigen in preferably nonionic detergent followed by the addition of Quillaja saponins, e.g., QS-21 and QS-7, a sterol, e.g., cholesterol, and phosphatidylcholine. In the presence of amphipathic antigen, ISCOM particles are formed on removal of the detergent. If no antigen is present in the mixture, ISCOM matrix is formed. ISCOM-borne antigen induces an enhanced, cell-mediated immune response, delayed type hypersensitivity reaction, and cytotoxic T-lymphocyte (CTL) response under MHC class I restriction.

The saponin compositions of the present invention may also be encapsulated within polymeric microspheres. For example, polymeric microspheres, such as poly(lactic-coglycolic) acid (PLGA), have been shown to be a compatible combination with QS-21 (Cleland, J. L. et al., *AIDS Res. Hum. Retroviruses* 10(S2):S21 (1994).

Saponins have also been combined with liposomes and liposomes prepared from natural and synthetic lipids according to U.S. Pat. No. 4,235,877 to Fullerton. Also, liposomes containing intercalated Quil A have been used as vehicles for hydrophilic antigens (Lipford, G. B. et al., *Vaccine* 12(1):73 (1994).

The saponin compositions of the present invention may also be used in a kit for the immunization of an individual comprising a carrier compartmentalized to receive in close confinement therein one or more container means wherein a first container contains a saponin composition of he invention. The kit may also include at least one other container means which contain a saponin adjuvant or other adjuvant as described herein.

Having now generally described the invention, the same may be further understood by reference to the following examples, which are not intended to be limiting unless so expressly stated.

EXAMPLE 1

Purification of QS-21 and QS-7 Intermediates by Silica Chromatography 20 grams of lyophilized, dialyzed *Quillaja saponaria* extract was dissolved in 150 mls of a mixture of 62% chloroform, 32% methanol, 6% water, and 0.23% acetic acid (v/v/v/v). A total volume of 100 ml was loaded onto a 10 cm diameter column loaded with 450 g silica (EM LICROPREP, Si 60, 40–63 micron) in the same solvent mixture. The separate QS-21 and QS-7 fractions were identified by reversed-phase HPLC analysis, pooled, and dried by rotary evaporation followed by lyophilization. The total yield of QS-21 intermediate was 3.2 grams of approximately 51% purity by reversed phase BPLC. QS-7 eluted in a later fraction (0.66 grams of 17% purity).

EXAMPLE 2

Purification of Substantially Pure QS-21 by C18 Chromatography

QS-21 intermediate, prepared in Example 1, was further purified by preparative reversed phase HPLC on a Vydac C18 column (10 micron particle size, 300 angstrom pore size, 25 cm length, 2.2 cm diameter). A 100 mg/ml solution of QS-21 intermediate was prepared in 38% acetonitrile/ 62% water/0.15% trifluoroacetic acid (v/v/v). A 20 mg aliquot was then separated on the Vydac column under isocratic chromatographic conditions in 38% acetonitrile/ 62% water/0.15% trifluoroacetic acid. Sixteen chromatography runs under identical isocratic chromatography runs were carried out. Fractions that yielded substantially pure QS-21 (from in-process reversed phase HPLC analysis) were collected and pooled for a total volume of 930 ml. This was diluted to 1860 ml by the addition of HPLC grade water. The diluted pool was loaded onto a Vydac C18 column (20–30 micron, 15 cm length×2.5 cm internal diameter) equilibrated in water. The diluted pool was loaded onto the column at 10 ml/minute, run in 100% water for an additional 30 minutes at 10 ml/minute, and then the QS-21 was eluted with a linear gradient from 100% water to 100% methanol over 60 minutes. The QS-21 eluted as a single peak. The QS-21/methanol/water mixture was transferred to a lyophilization flask, evaporated under a steady stream of nitrogen to remove methanol, and freeze-dried. The final yield was 59 mg of QS-21 of approximate 98% purity.

EXAMPLE 3

Alternative Method for Obtaining Substantially Pure QS-21

A suitable aqueous extract of *Quillaja saponaria* is adsorbed to polyvinylpolypyrrolidone (PVPP) at a ratio of 120 grams of PVPP per liter of 10% extract (w/v). The PVPP binds and separates tannins and polyphenolics from the soluble saponin fraction. The PVPP is removed by an appropriate method such as centrugation or filtration. This is then followed by membrane filtration of the treated extract to remove small particulates. A sample is analyzed via in-process HPLC analysis and comparison to a QS-21 standard curve for determination of QS-21 concentration.

The saponins in the PVPP-treated extract are further concentrated by ultrafiltration (through a 30,000 dalton molecular weight cutoff membrane) to an approximate concentration of 8 to 12 grams per liter. The retentate, containing the saponin fraction, is then diafiltered against 5 volumes of purified water. The diafiltration retentate is then collected, analyzed for QS-21 content by in-process reversed-phase HPLC analysis, and is diluted to a final QS-21 concentration of 7 to 9 grams per liter. The actual QS-21 concentration is determined at this point by in-process HPLC analysis and comparison to a QS-21 standard curve for determination of QS-21 concentration.

This extract is then diluted by addition of acetonitrile to a final 30% acetonitrile (v/v) concentration, centrifuged at 10,000×g for 30 min, and the precipitate is discarded. The filtered supernatant is further purified by consecutive preparative HPLC runs on a phenyl HPLC resin in a stainless steel column (25 cm length column with an additional 5 cm length guard column) equilibrated in a solvent consisting of 30% acetonitrile, 70% water, and 0.2% acetic acid. The QS-21 peak is eluted by running a linear gradient from 30% to 39% acetonitrile over 19 column volumes followed by a linear gradient from 39% to 90% acetonitrile over 1 column volume. The fractions containing QS-21 are collected. This step yields QS-21 of approximately 60–75% purity.

This QS-21 fraction is further purified by repetitive, automated preparative HPLC on a phenyl HPLC resin (spherical) packed into a stainless steel column (25 cm length with a 5 cm length guard column) and equilibrated in 20% acetonitrile, 0.2% acetic acid. The QS-21 peak is eluted with a linear gradient from 20 to 28% acetonitrile, 0.2% acetic acid over 1.7 column volumes followed by a linear gradient from 28% to 35% acetonitrile over 3.3 column volumes followed by a linear gradient from 35% to 38.5% acetonitrile over 14 column volumes. The fractions containing QS-21 are collected.

The QS-21 pool is diluted by addition of a minimum of 0.5 volumes of HPLC grade water. The QS-21 fraction is adsorbed to a column of 10 cm length containing C8 resin (15–25 micron particle size). The column is rinsed with at least one column volume of water. QS-21 is eluted from the resin by a linear methanol gradient 90 to 100%. The QS-21 eluate is collected, evaporated to near dryness in a rotary evaporator under vacuum, and dried further on a lyophilizer. The QS-21 powder is then resuspended in a small volume of HPLC grade water (8 to 12 g QS-21 per 100 ml water) and relyophilized to dryness. The final product is $\geq 98\%$ pure by reversed-phase HPLC.

EXAMPLE 4

Purification of Substantially Pure QS-7 by C18 Chromatography

QS-7 intermediate, prepared as described in Example 1, was further purified on a Waters C18 column. A 100 mg/ml solution of QS-7 intermediate was dissolved in water. Twenty mg of this solution was eluted on C18 (0.78 cm ID×30 cm length, 10 micron) in a linear gradient of 80% water/20% acetonitrile/0.15% trifluoroacetic acid to 40% water/60% acetonitrile/0.15% trifluoroacetic acid over 75 minutes at a 2 ml/minute flow rate. A total of four runs were made and the QS-7 fractions were combined for a total of 19 mg of approximate 54% purity. This preparation was dissolved at 4 mg/mi in water and further purified by isocratic HPLC on the same column, equilibrated in 67% water/33% acetonitile/0.15% trifluoroacetic acid. The collected fractions were diluted with an equal volume of water and adsorbed to C18 resin (20–30 micron) in a Buchner funnel, and washed with 90 ml water. The QS-7 was then eluted with 40 ml methanol. The methanol was evaporated under a stream of nitrogen, the QS-7 was redissolved in water, and lyophilized, yielding a total of 8 mg of purified QS-7.

Other reversed phase resins, solvents, and separation gradients have been shown to be suitable for purification of QS-7 and QS-21 as well as other saponins from *Q. saponaria* (Kensil, *J. Immunol.* 146:431–437 (1991)).

EXAMPLE 5

Alternative Method for Obtaining Substantially Pure QS-7

QS-7 can be obtained from diafiltered, PVPP-treated *Quillaja saponaria* extract which is then adjusted to 25% acetonitrile/75% water/0.2% acetic acid (v/v/v). This extract is further purified by consecutive preparative HPLC runs on a phenyl HPLC resin (10 micron particle size, 100 angstrom pore size) in a stainless steel column (25 cm length column) equilibrated in a solvent consisting of 20% acetonitrile, 75% water, and 0.2% acetic acid. The QS-7 peak is eluted by running a linear gradient from 25% to 36% acetonitrile over 11 column volumes. The QS-7 fractions are collected. This step yields QS-7 of approximately 50 to 60% purity.

The pool from these column runs is then diluted to 28% acetonitrile/72% water/0.2% acetic acid by addition of 0.2% acetic acid in water (v/v). The QS-7 fraction is then further purified by isocratic chromatography on C8 HPLC resin (10 micron particle size, 100 angstrom pore size in a 25 cm length column) equilibrated in a solvent consisting of 31% acetonitrile/69% water/0.2% acetic acid (v/v/v). The QS-7 fractions are collected.

The QS-7 fraction is diluted by addition of 2 volumes of water for injection. The QS-7 fraction is adsorbed to a column of 10 cm length containing C8 resin (15–25 micron particle size). A linear gradient of 5 to 50% t-butyl alcohol is used to elute QS-7 from the column. The fractions containing QS-7 are collected. These fractions are directly lyophilized to yield a white powder. This process yields a QS-7 of ≧95% purity by reversed-phase HPLC.

EXAMPLE 6

Characterization of QS-7 and QS-21 by Mass Spectrometry

Figure 2A:
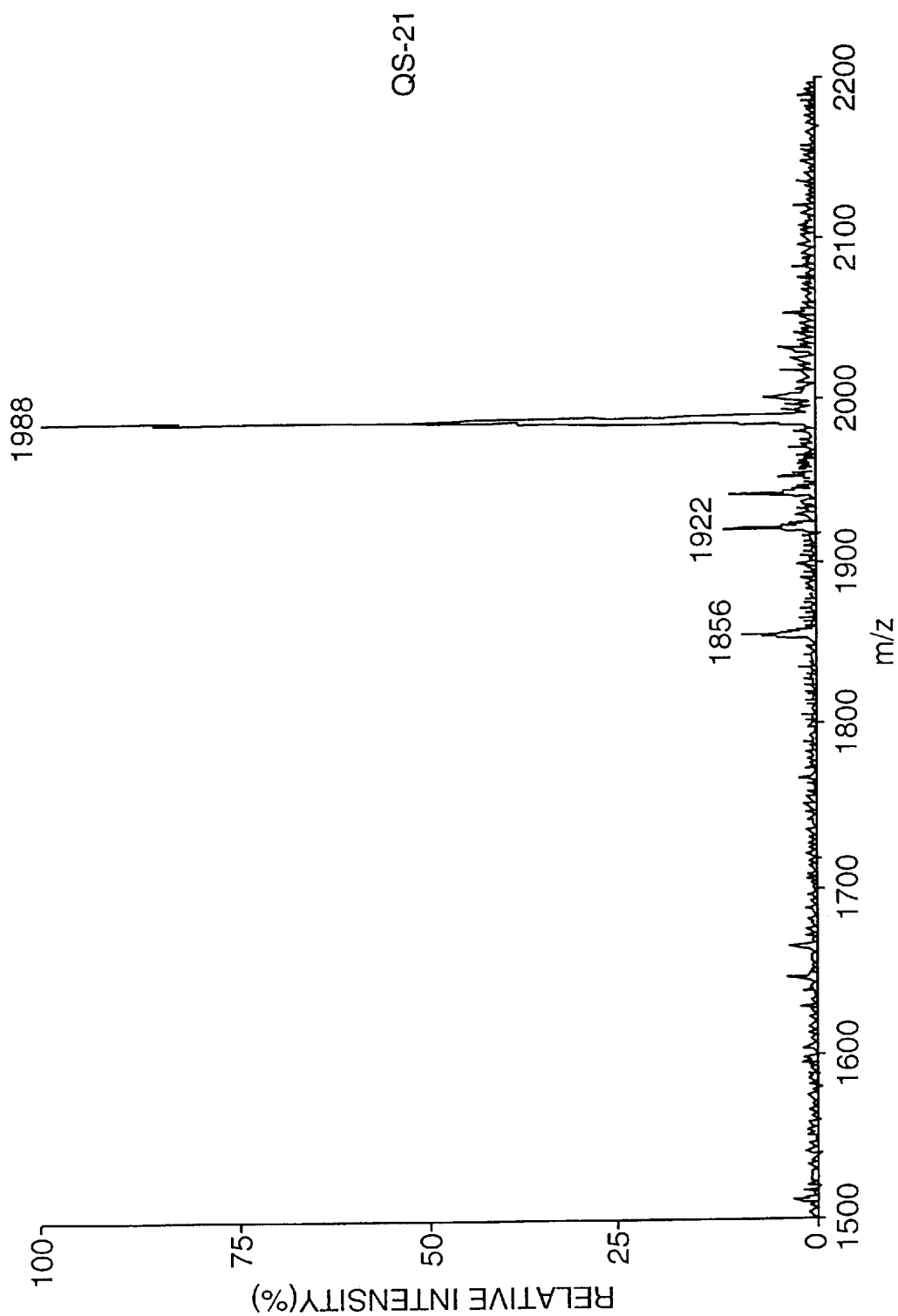
FIG. 2, Panel A, shows the analysis of QS-21 by fast atom bombardment mass spectroscopy in the negative mode. The predominant pseudomolecular ion is 1988, corresponding to $m/z=[M-H]^-$ where $M=C_{92}O_{46}H_{148}$. Panel B shows the spectrum of the QS-7 peak by fast atom bombardment mass spectrometry. The predominant pseudomolecular ion is 1862, corresponding to $[M-H]^-$. One formula consistent with this structure is $C_{83}O_{46}H_{130}$.
Figure 2B:
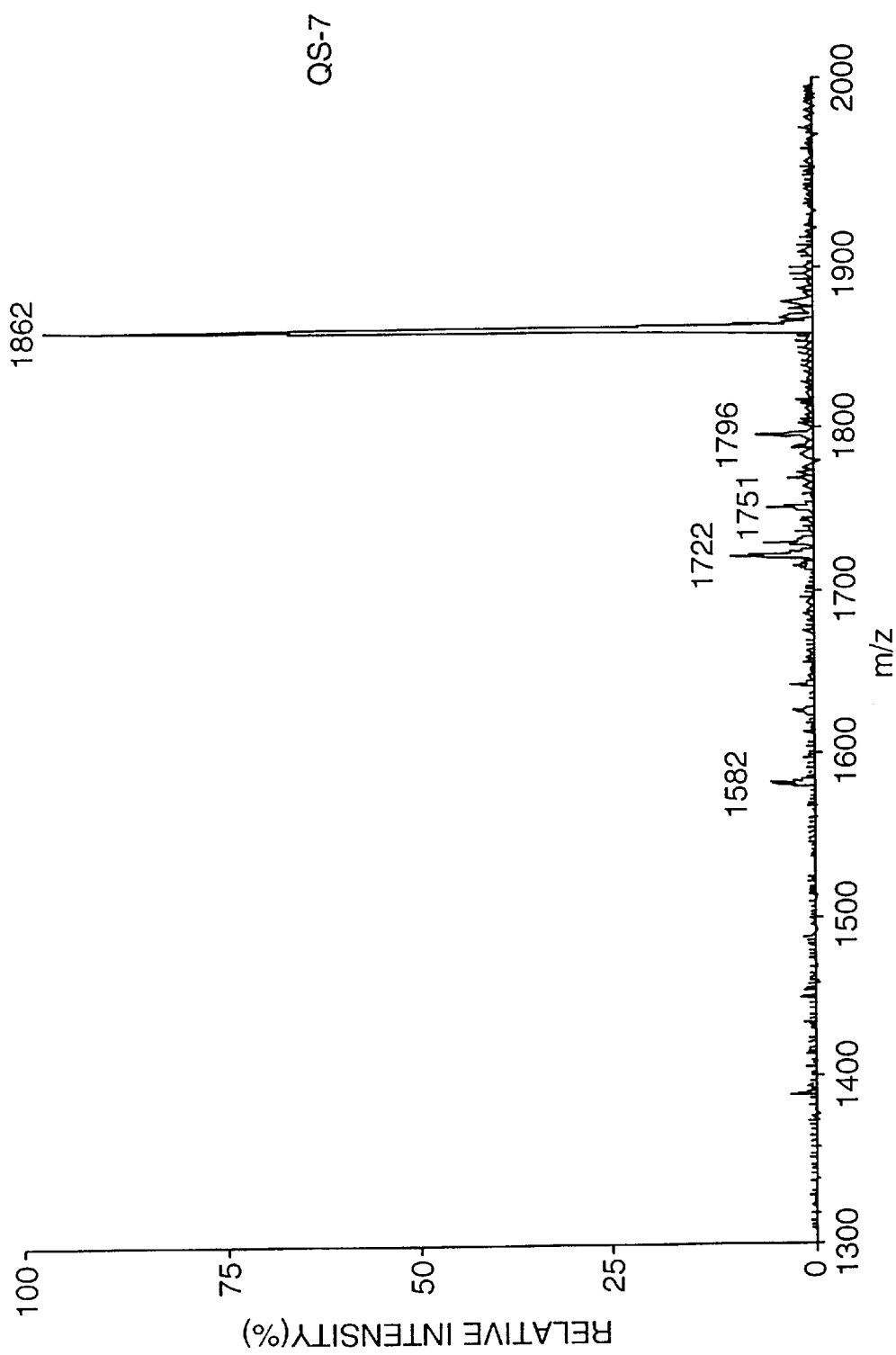

Distinct saponins can be identified by mass spectrometry. FIG. 2A shows the analysis of QS-21 by fast atom bombardment mass spectroscopy in the negative mode. The predominant pseudomolecular ion is 1988, corresponding to m/z=[M-H]$^-$ where M=$C_{92}O_{46}H_{148}$. FIG. 2B shows the spectrum of the QS-7 peak by fast atom bombardment mass spectrometry. The predominant pseudomolecular ion is 1862, corresponding to [M-H]$^-$. One formula consistent with this structure is $C_{83}O_{46}H_{130}$.

Figure 3A:
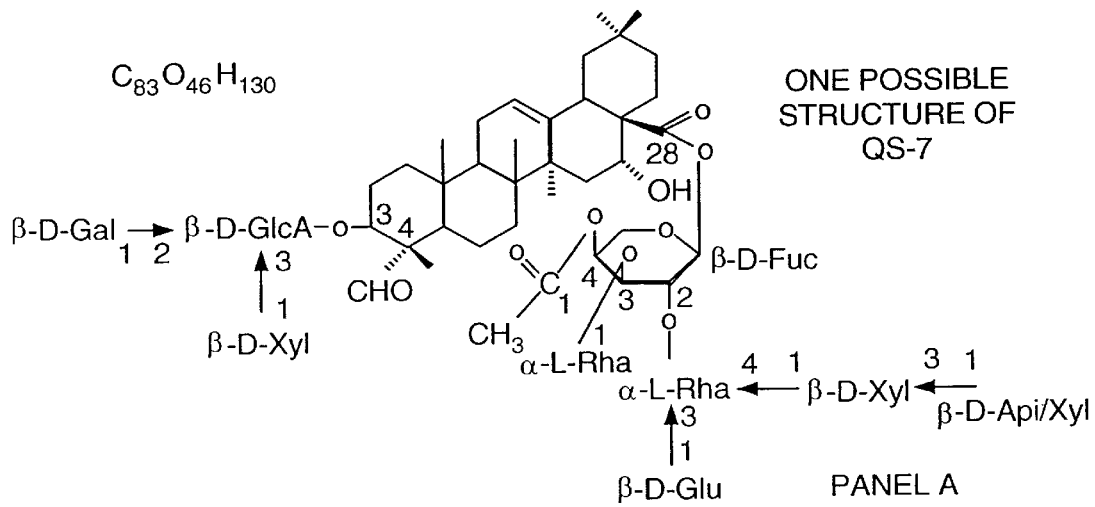
FIG. 3, Panel A, shows the proposed structure of QS-7. Panel B shows the structure for QS-21 as determined by 2-D $^1H$ and $^{13}C$-N. The variation between the individual components QS-21-V1 and QS-21-V2 is indicated by the alternative terminal β-D-apiose (QS-21-V1) or β-D-xylose (QS-21-V2) residues (Panel B).
Figure 3B:
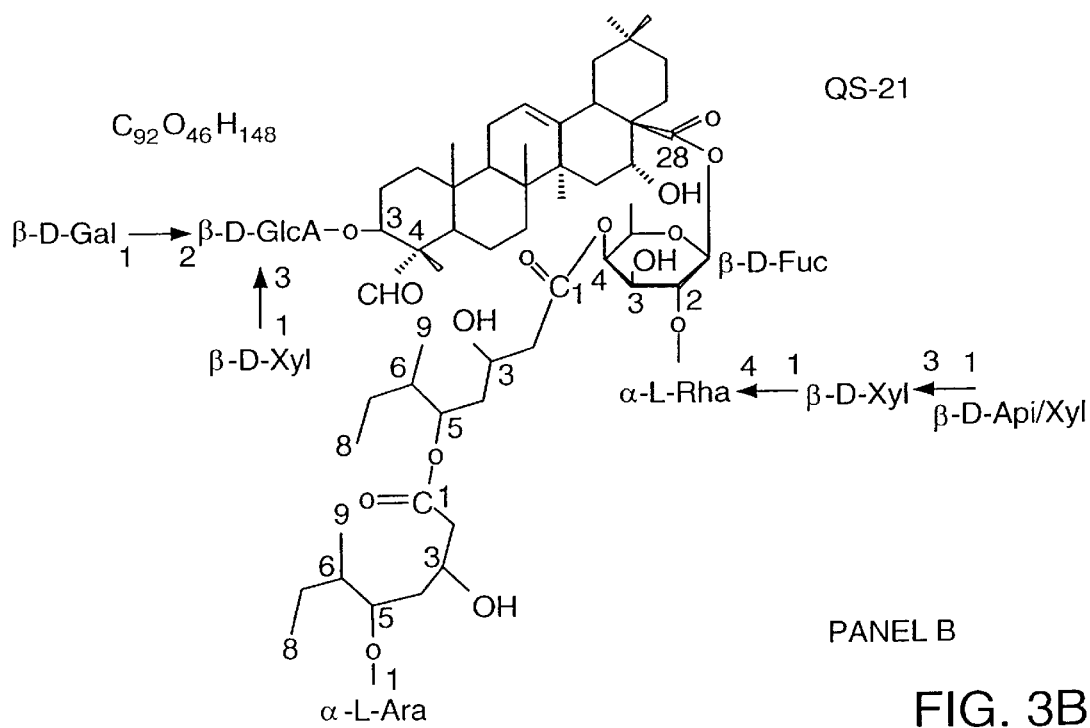

The saponins from *Q. saponaria* are acylated bisdesmodic triterpene glycosides. The structure of QS-21 has been determined by 2-D $^1$H and $^{13}$C-NMR Jacobsen, N. E. et al., *Carbohydrate Research*, Volume 280:1–14 (1996)). This structure is shown in FIG. 3B. A proposed structure for QS-7 is shown in FIG. 3A.

EXAMPLE 7

Synergistic Adjuvant Effect of Coadministration of QS-7 and QS-21

Immunologic compositions comprising one or more substantially pure *Quillaja saponaria* saponin fractions and methods of using such compositions as immune adjuvants were previously disclosed in Kensil et al U.S. Pat. No. 5,057,540 and in copending U.S. patent application Ser. No. 07/906,880 (allowed with issue fee paid, to issue as U.S. Pat. No. 5,583,112), the entire disclosures of which are hereby incorporated by reference. Kensil, C. R. et al., *Vaccine* 2:273–281 (1993) teaches that doses below 2.5 μg QS-21 are ineffective as adjuvants for raising an antibody response to the ovalbumin antigen in mice. Similarly, Newman, M. et al., *J. Immunol.* 148:2357–2362 (1992) shows a corresponding QS-21 dose response curve for the cytotoxic T lymphocyte (CTL) response to ovalbumin. Again, at 2.5 μg or lower, the response in mice is minimal.

The present inventors have now discovered that two substantially pure saponins unexpectedly produce a synergistic adjuvant effect when combined in suboptimal doses.

The two saponins which produce a synergistic response when combined at suboptimal doses are QS-7 and QS-21. Briefly, five mixtures of suboptimal doses of QS-7 and QS-21 were tested for their ability to produce a synergistic response. It was expected that the effect would be an additive adjuvant effect.

All experiments were carried out in C57BL/6 mice (female, 8–12 weeks of age). The synergistic adjuvant-effect of the QS-21/QS-7 mixtures was assessed by two parameters: (1) the ability of these mixtures to improve antibody titers to a subunit antigen, ovalbumin, in mice; and (2) the ability of these mixtures to improve an ovalbumin-specific cytotoxic T lymphocyte (killer cell) response in mice.

The experimental techniques were the following. The mice were immunized subcutaneously at week 1, 3, and 0.2 ml of the indicated formulations in phosphate-buffered saline, Mice were immunized in groups of five. Sera and spleens were harvested at weeks 7 to 9. Sera was assayed for anti-ovalbumin antibody response by enzyme immunoassay. Briefly, a 96 well Immulon plate was coated with 10 μg/ml ovalbumin in phosphate-buffered saline (PBS) overnight at 4° C. These plates were blocked with 10% normal goat serum in PBS (diluent) for one hour at room temperature. Serial 1:10 dilutions of serum were made in diluent and were incubated on the plates for one hour at room temperature or overnight at 4° C. An enzyme conjugate of anti-mouse IgG (or anti-mouse IgG subclass) was diluted in diluent and incubated on the plate. A colorimetric enzyme substrate, tetramethylbenzidine, was used to assay for binding of anti-ovalbumin antibody. Spleens from immunized mice were used to assay for the cytotoxic T lymphocyte (CTL) response. The effector cells for the (CTL) assay were splenic mononuclear cells from the harvested spleens. The antigen-positive target cells for the assay were E.G7-OVA cells, which are an MHC class II antigen-negative EL4 mouse cell line, transfected with the ovalbumin gene. This cell line expresses an ovalbumin peptide on MHC Class I antigen and hence is a target for ovalbumin-specific cytotoxic T lymphocytes (Moore, M., et al., *Cell* 54: 777 (1988)). EL4 cells were used as an ovalbumin-negative target cell line. Prior to assay, splenic mononuclear cells were stimulated with antigen to induce maturation of precursor CTL in the effector cell population. The antigens used for stimulation were mitomycin C treated E.G7-OVA cells (incubated with spleen cells at a ratio of 20:1 spleen cells: E.G7-OVA cells) or denatured ovalbumin (25 μg/ml). Bulk cell culture was carried out in a 2 ml volume at $10^6$/ml, using supplemented RPMI 1640 medium, at 37° C. Cells were recovered after a six day culture, resuspended in fresh media, and used in the CTL assay. Target cells (E.G7-OVA or EL4) were prepared for the CTL assay by labeling with $Na_2CrO_4$ ($^{51}$Cr) by incubation for 1 hour at 37° C. in RPMI 1640 culture media with 0.3M sucrose. A standard cytotoxicity assay was used with $10^4$ target cells per well and a titration of effector target ratios of 25:1, 12:1 6:1, and 3:1. The experimental data was converted to % lysis. The % of lysis of EL4 cells was subtracted from the lysis of E.G7-OVA cells to determine the % of antigen-specific lysis.

Figure 4:
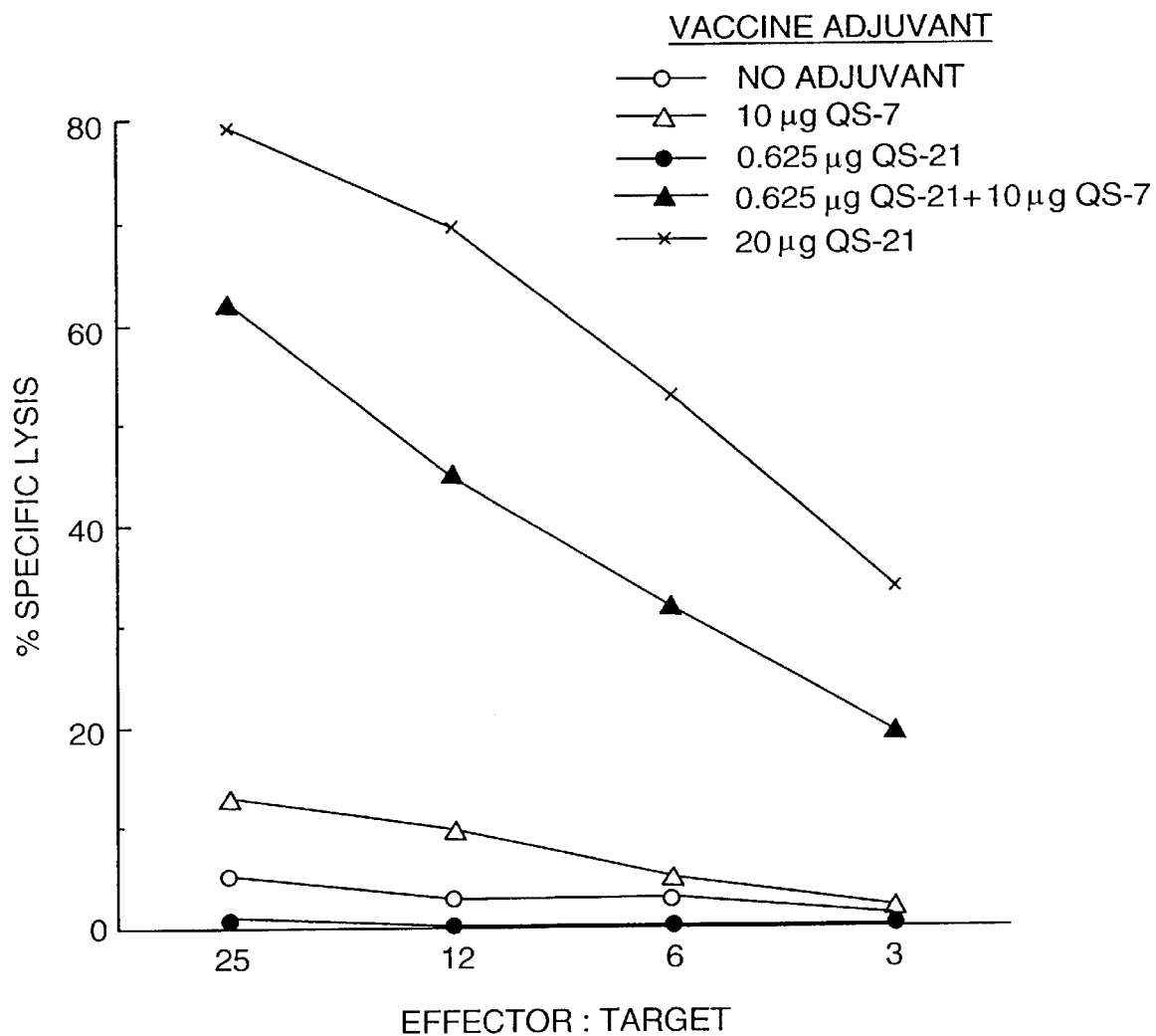
FIG. 4 shows the cytotoxic T-lymphocyte mediated lysis of E.G7-OVA target cells induced by the combination of suboptimal doses of QS-21 (0.625 µg) and QS-7 (10 µg) compared to the CTL response induced by identical doses of these saponins administered individually. The optimal response induced by 20 µg of QS-21 is also shown for comparison.
Figure 5:
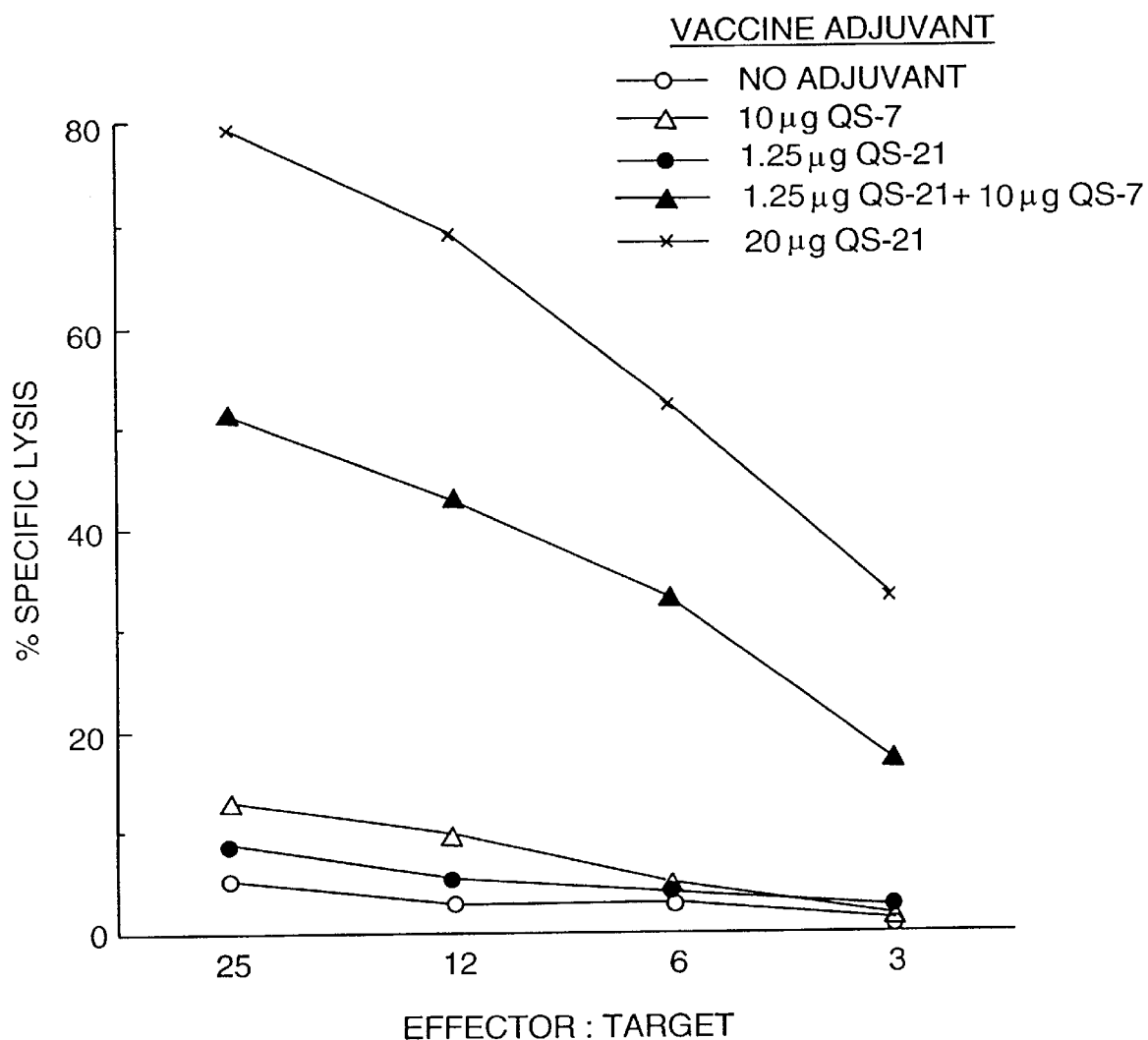
FIG. 5 shows the cytotoxic T-lymphocyte mediated lysis of E.G7-OVA target cells induced by the combination of suboptimal doses of QS-21 (1.25 µg) and QS-7 (10 µg) compared to the CTL response induced by identical doses of these saponins administered individually. The optimal response induced by 20 µg of QS-21 is also shown for comparison.
Figure 6:
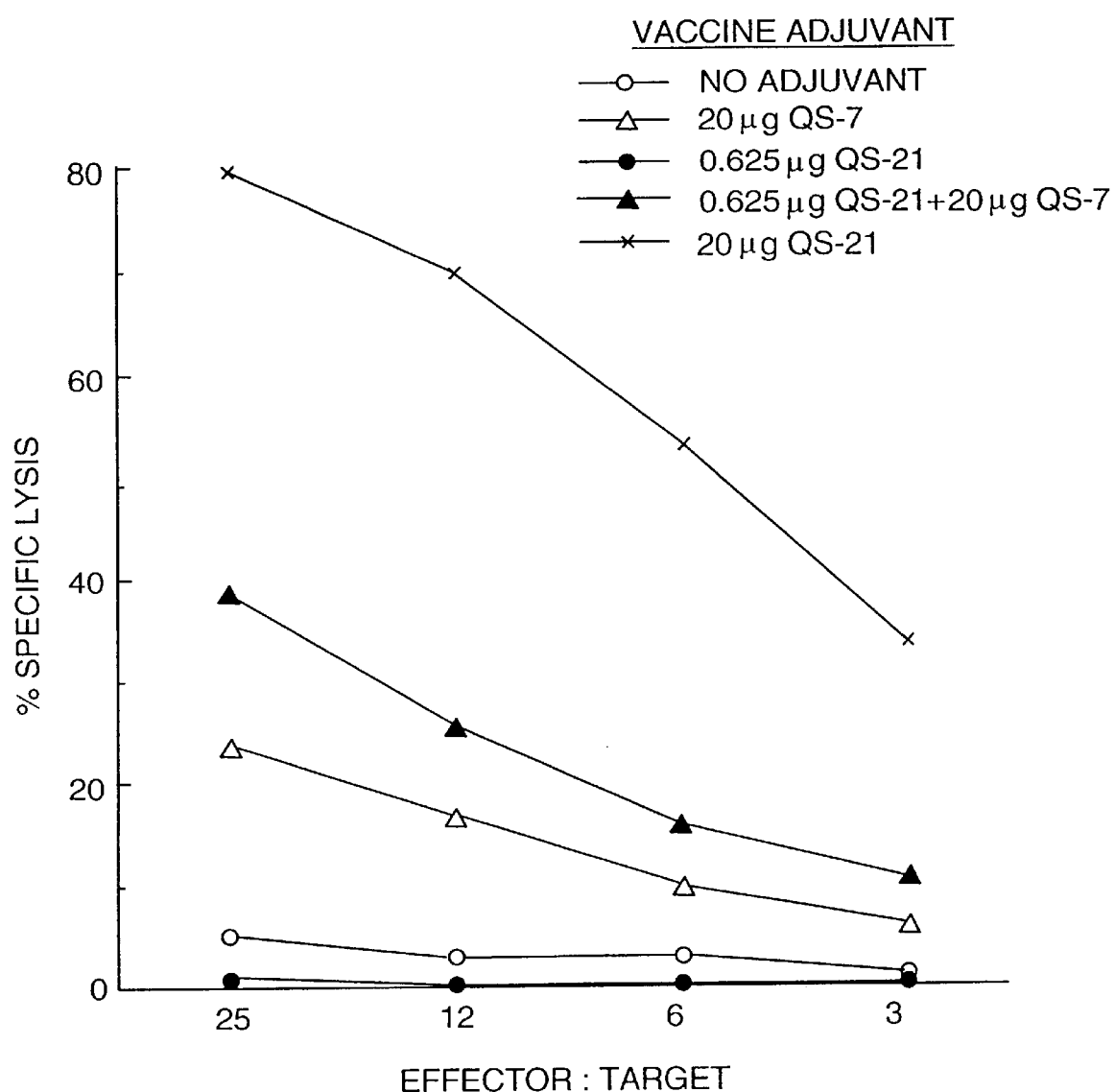
FIG. 6 shows the cytotoxic T-lymphocyte mediated lysis of E.G7-OVA target cells induced by the combination of suboptimal doses of QS-21 (0.625 µg) and QS-7 (20 µg) compared to the CTL response induced by identical doses of these saponins administered individually. The optimal response induced by 20 µg of QS-21 is also shown for comparison.
Figure 7:
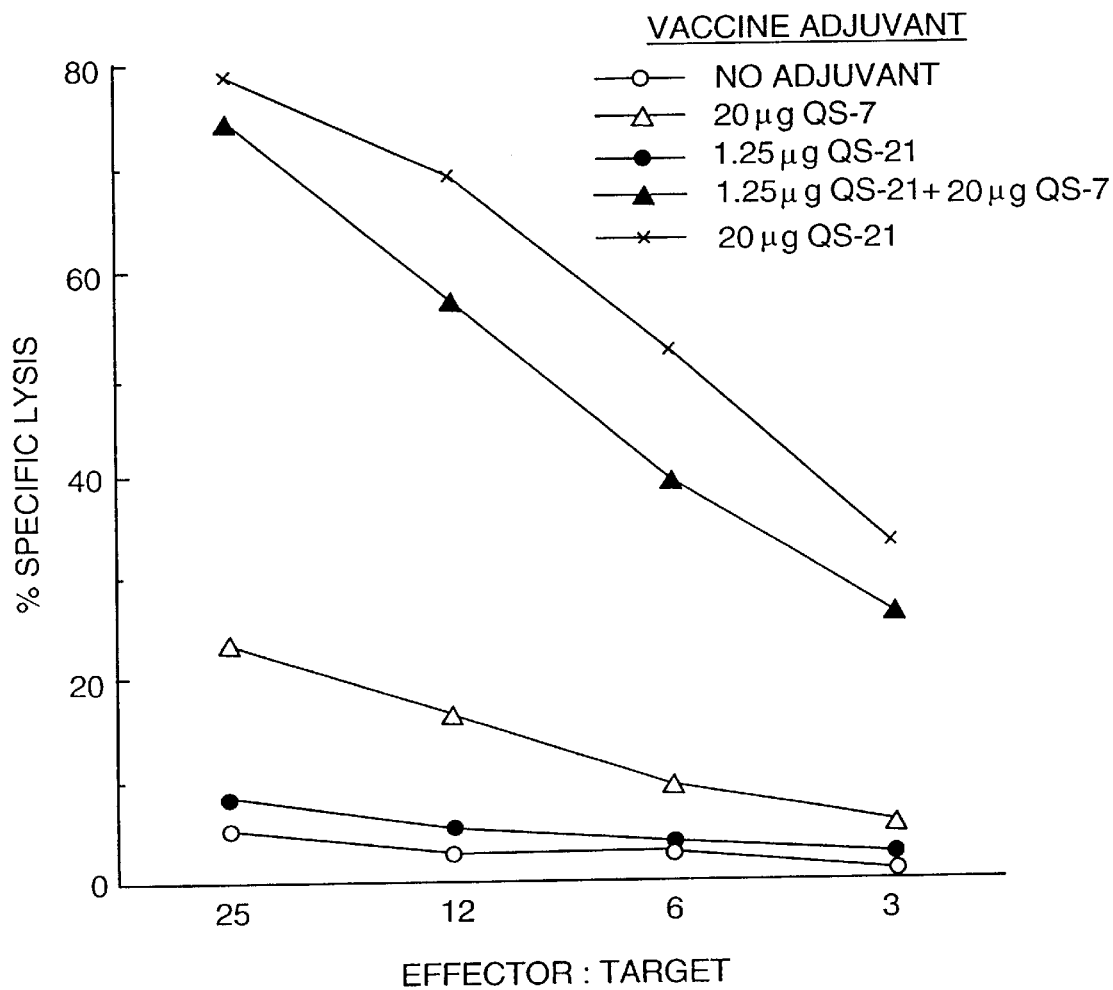
FIG. 7 shows the cytotoxic T-lymphocyte mediated lysis of E.G7-OVA target cells induced by the combination of suboptimal doses of QS-21 (1.25 µg) and QS-7 (20 µg) compared to the CTL response induced by identical doses of these saponins administered individually. The optimal response induced by 20 µg of QS-21 is also shown for comparison.

First, suboptimal doses of the saponin adjuvants QS-7 and QS-21 were identified. FIGS. 4 and 5 show that 0.625 μg and 1.25 μg of QS-21 are ineffective in stimulating a CTL response. In contrast, a dose of 20 μg of QS-21 is highly effective in stimulating a CTL response. FIGS. 4 and 5 show that 10 and 20 μg of QS-7 are ineffective in stimulating a strong CTL response.

These suboptimal doses of QS-21 and QS-7 were then combined as follows:

| mixture | QS-21 | QS-7 |
|---|---|---|
| 1 | 0.625 μg | 10 μg |
| 2 | 1.25 μg | 10 μg |
| 3 | 0.625 μg | 20 μg |
| 4 | 1.25 μg | 20 μg |

Unexpectedly, these mixtures yielded considerably higher cytotoxic T-lymphocyte responses than predicted by simple addition of the response to the doses of QS-21 and QS-7. The response is most dramatic at the lower dose of QS-7 (10 μg). The response for these four mixtures is shown in FIGS. 4–7.

Figure 8:
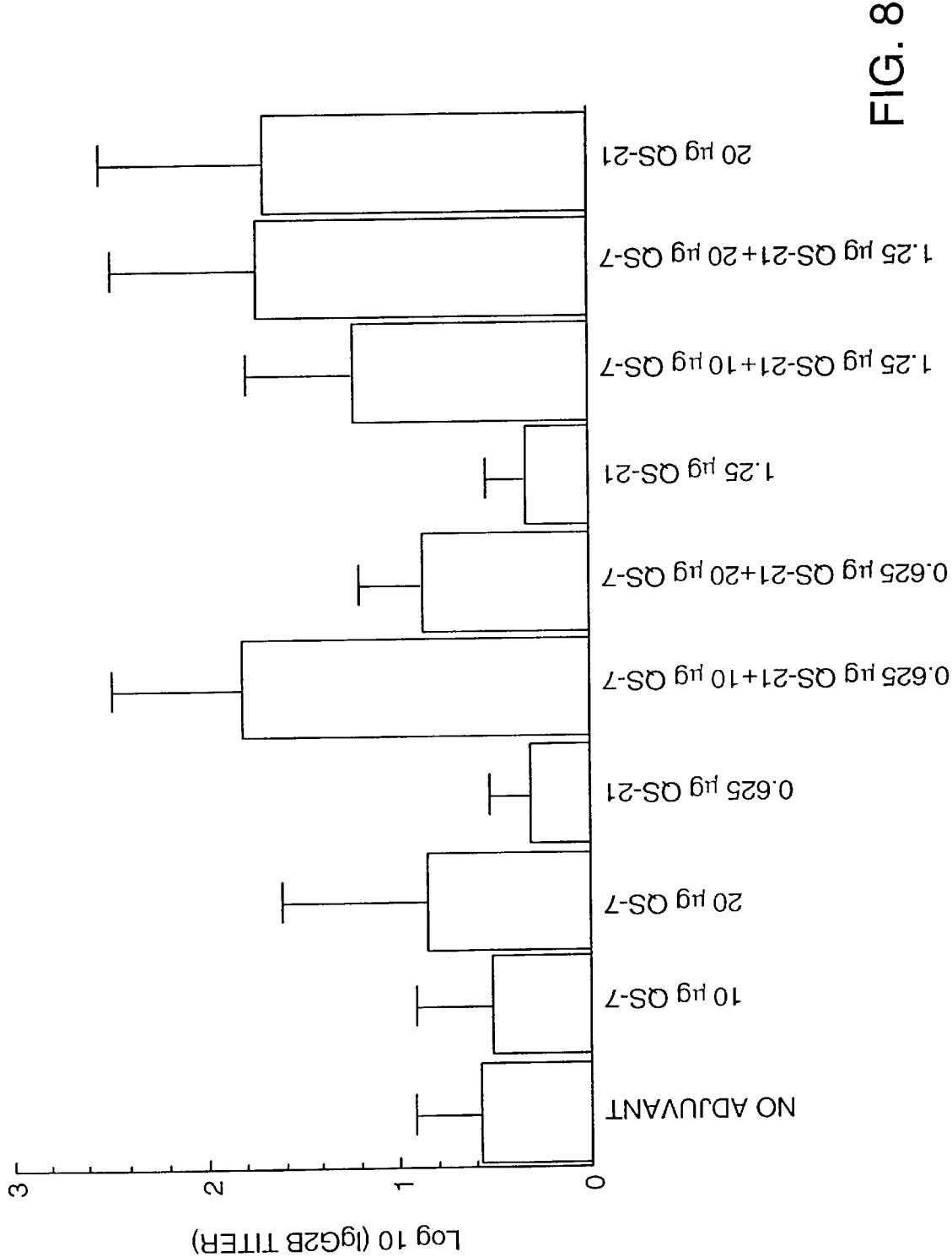
FIG. 8 shows the mean log 10 titer from an average of five mice receiving these mixtures, compared to suboptimal individual doses.

These mixtures also yielded unexpectedly higher antibody titers to ovalbumin, particularly in the IgG2b subclass. The mean log 10 titer from an average of five mice receiving these mixtures, compared to suboptimal individual doses, is shown in FIG. 8. For example, neither 10 μg QS-7 or 0.625 μg QS-21, individually, yields a titer that is higher than no adjuvant, showing that these doses are suboptimal. However, the combination of 0.625 μg QS-21 with 10 μg of QS-7 yields an increase of 1 log 10 unit in titer (10 fold increase in titer), indicating that the combination of the two is an effective adjuvant mixture that yields a response comparable to a known optimal dose of QS-21 (20 μg).

Figure 9:
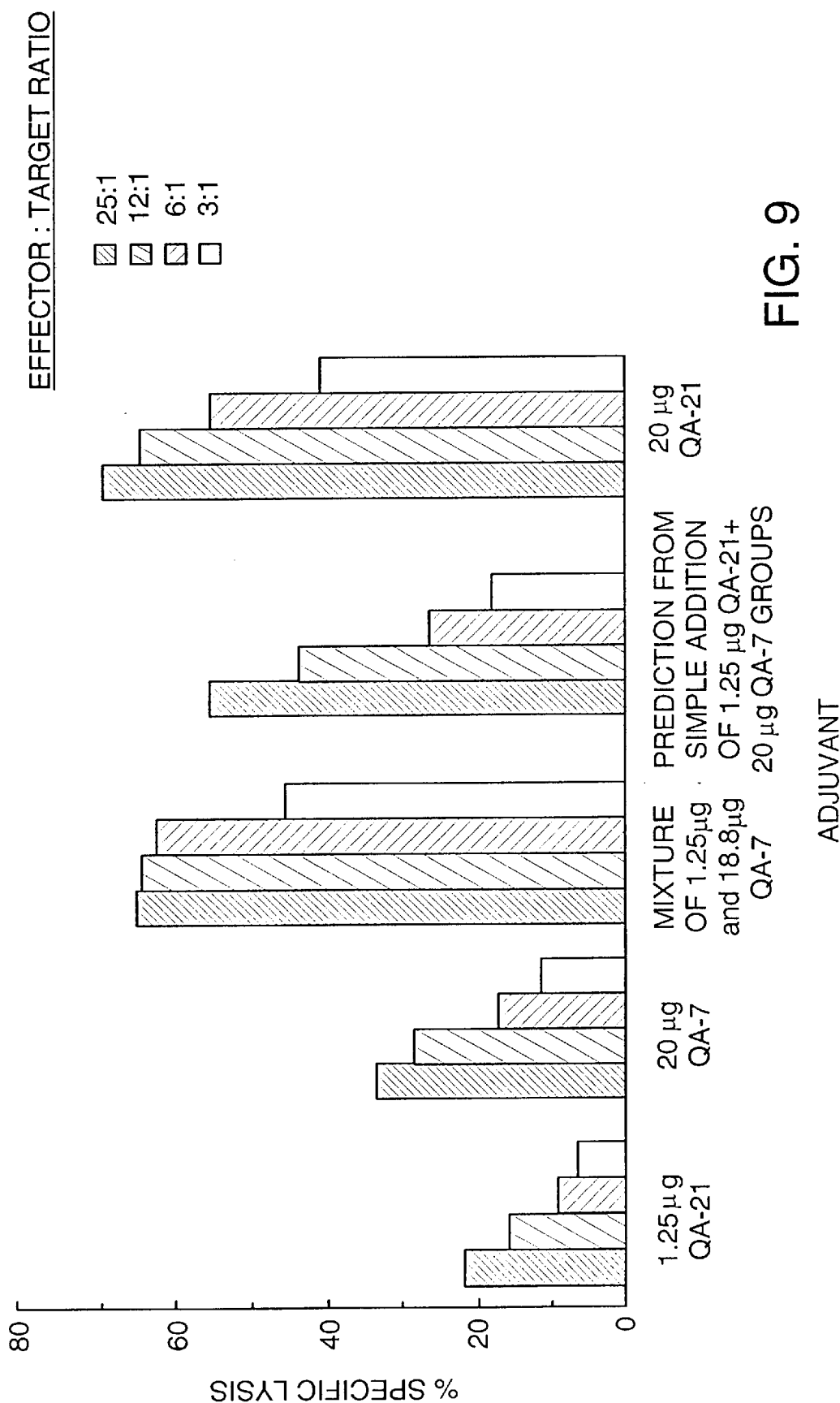
FIG. 9 shows the cytotoxic T-lymphocyte response to the combination of suboptimal doses of QS-21 (1.25 µg) and QS-7 (18.8 µg) compared to the 1.25 µg and 20 µg doses respectively of the same saponins administered individually, and to the predicted additive effect of the combination of QS-21 (1.25 µg) and QS-7 (20 µg). The optimal response induced by 20 µg of QS-21 is shown for comparison.
Figure 10:
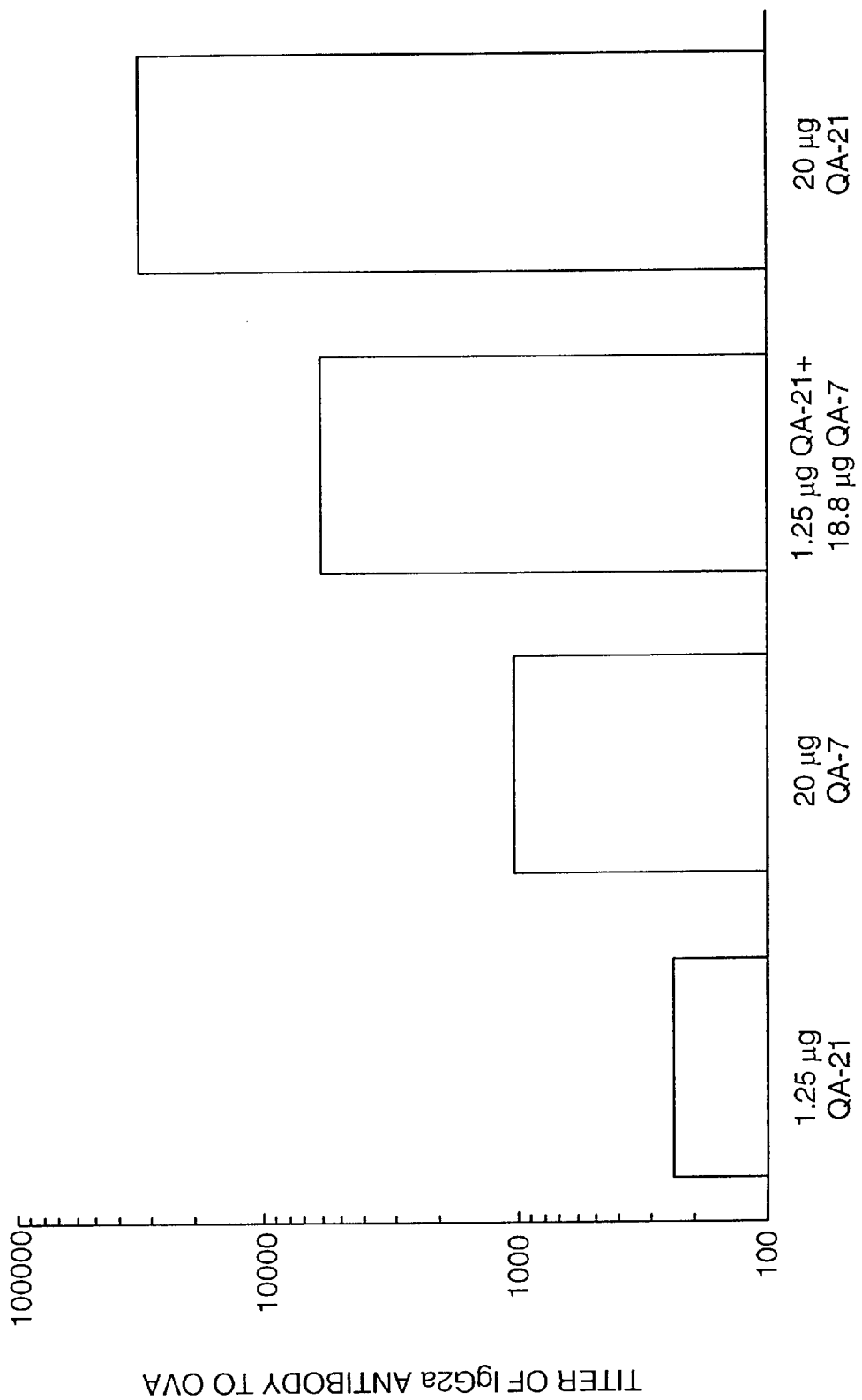
FIG. 10 shows the antibody response m serum of the combination of suboptimal doses of QS-21 (1.25 µg) and QS-7 (18.8 µg) compared to 1.25 µg and 20 µg doses respectively of the same saponins administered individually. The optimal response induced by 20 µg of QS-21 is shown for comparison.

The synergistic effect was also observed in another experiment using the same experimental model. In that experiment, a mixture of 1.25 μg of QS-21 and 18.8 μg QS-7 was compared to 1.25 μg QS-21 and 20 μg QS-7, respectively. The mixture produced a higher cytotoxic T-lymphocyte response and serum antibody response than predicted from these saponins alone (FIGS. 9–10).

What is claimed is:

1. A *Quillaja saponaria* saponin composition for eliciting an immune response in an organism, comprising a combination of a substantially pure QS-7 saponin and a substantially pure saponin selected from the group consisting of:
   (a) QS-17,
   (b) QS-18,
   (c) QS-21,
   (d) QS-21-V1, and
   (e) QS-21-V2,
   wherein the substantially purified saponins of the combination are present in suboptimal dosages for the organism, and
   wherein in the presence of an antigen, the combination has a synergistic adjuvant effect in eliciting the immune response.

2. The saponin composition of claim 1, wherein the substantially pure saponins comprise QS7 and QS-21.

3. The saponin composition of claim 1, wherein the substantially pure saponins comprise QS-7 and QS-21 V1.

4. The saponin composition of claim 1, wherein the substantially pure saponins comprise QS-7 and QS-21 V2.

5. The saponin composition of claim 1, wherein the substantially pure saponins comprise QS-7 and QS-17.

6. The saponin composition of claim 1, wherein the substantially pure saponins comprise QS-7 and QS-18.

7. A *Quillaja saponaria* saponin composition for eliciting an immune response in an organism, comprising a combination of a substantially pure QS-21-V1 saponin and a substantially pure saponin selected from the group consisting of:
   (a) QS-17, and
   (b) QS-18,
   wherein the substantially purified saponins of the combination are present in suboptimal dosages for the organism, and
   wherein in the presence of an antigen, the combination has a synergistic adjuvant effect in eliciting the immune response.

8. The saponin composition of claim 7, wherein the saponin composition comprises a substantially pure QS-21-V1 saponin and a substantially pure QS-17 saponin.

9. The saponin composition of claim 7, wherein the saponin composition comprises a substantially pure QS-21-V1 saponin and a substantially pure QS-18 saponin.

10. A *Quillaja saponaria* saponin composition for eliciting an immune response in an organism, comprising a combination of a substantially pure QS-21-V2 saponin and a substantially pure saponin selected from the group consisting of:
    (a) QS-17, and
    (b) QS-18,
    wherein the substantially purified saponins of the combination are present in suboptimal dosages for the organism, and
    wherein in the presence of an antigen, the combination has a synergistic adjuvant effect in eliciting the immune response.

11. The saponin composition of claim 10, wherein the saponin composition comprises a substantially pure QS-21-V2 saponin and a substantially pure QS-17 saponin.

12. The saponin composition of claim 10, wherein the saponin composition comprises a substantially pure QS-21-V2 saponin and a substantially pure QS-18 saponin.

* * * * *